US007638498B2

(12) United States Patent
Escher et al.

(10) Patent No.: US 7,638,498 B2
(45) Date of Patent: Dec. 29, 2009

(54) SUBSTANCES FOR PREVENTING AND TREATING AUTOIMMUNE DISEASES

(75) Inventors: Alan P. Escher, Redlands, CA (US); Fengchun Li, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 252 days.

(21) Appl. No.: 11/836,661

(22) Filed: Aug. 9, 2007

(65) Prior Publication Data

US 2008/0171714 A1    Jul. 17, 2008

Related U.S. Application Data

(62) Division of application No. 10/523,655, filed as application No. PCT/US03/24625 on Aug. 6, 2003, now Pat. No. 7,381,711.

(60) Provisional application No. 60/401,652, filed on Aug. 6, 2002.

(51) Int. Cl.
*A61K 48/00* (2006.01)
*C12N 15/85* (2006.01)

(52) U.S. Cl. .................... 514/44 R; 435/320.1; 435/455

(58) Field of Classification Search .................. 514/44; 435/320.1, 455
See application file for complete search history.

(56) References Cited

FOREIGN PATENT DOCUMENTS

WO    WO 00/59538 A    12/2000

OTHER PUBLICATIONS

Rabinovitch et al. (1999) Diabetes, vol. 48(6), 1223-1229.*
Borner et al. (1994) J. Cell Biol., vol. 126(4) 1059-1068.*
Allison et al. (2000) Int. Immunol., vol. 12(1), 9-17.*
Strasser et al. (1991) PNAS, vol. 88, 8661-8665.*
Mathisen and Touhy (2000) J. Clin. Immunol., vol. 20(5), 327-333.*
Trucco et al. (2002) Curr. Gene Ther., vol. 2, 341-354.*
Simone et al. (1999), Diabetes Care, vol. 22 (2), B7-B15.*
EPO Search Report, Nov. 29, 2005.
Borner C. et al., J. Cell Biol., Aug. 1994, vol. 126, No. 4, pp. 1059-1068.
Contreras, Juan et al., Cytoprotection of Pancreatic Islets Before and Early After Transplantation Using Gene Therapy, Kidney International, Jan 2002, vol. 61, No. 1 Suppl., pp. 79-84.
Contreras, Juan et al., Gene Transfer of the Bcl-2 Gene Confers Cytoprotection to Isolated Adult Porcine Pancreatic Islets Exposed to Xenoreactive Antibodies and Complement, Surgery, Aug. 2001, vol. 130, No. 2, pp. 166-174.
Efrat S. et al., Diabetes, May 2001, vol. 50, No. 5, pp. 980-984.
Filippova M. et al., Effects of Plasmid DNA Injection on Cyclophosphamide-Accelerated Diabetes in NOD Mice, DNA and Cell Biology, New York, NY, US vol. 20, No. 3, Mar. 1, 2001, pp. 175-181.
Ilan Y. et al., Proc. Natl. Acad. Sci. USA, Mar. 1997, vol. 94, pp. 2587-2592.
Li A. F. et al., Co-Delivery of Pro-Apoptotic BAX With a DNA Vaccine Recruits Dendritic Cells and Promotes Efficacy of Autoimmune Diabetes Prevention in Mice, Vaccine, Butterworth Scientific Guildford, GB, vol. 22, No. 13-14, Apr. 16, 2004, pp. 1751-1763.

Rabinovitch, A. et al., Diabetes, Jun. 1999, vol. 48, No. 6., pp. 1223-1229.
Tokui M. et al., Studies on the Prevention of Diabetes in NOD Mice by Intramuscular Adminstration of Plasmic Expressing GAD and IL-4, Chemical Abstracts + Indexes, American Chemical Society, Columbus, OH, US, vol. 25, No. 125, 1996, p. 1148.
Balasa, B. et al., "Vaccination with glutamic acid decarboxylase plasmid DNA protects mice from spontaneous autoimmune diabetes and B7/CD28 costimulation circumvents that protection," Clin. Immunol., 2001, vol. 99, No. 2, pp. 241-252.
Chao, D. T. et al., BCL-2 family : regulators of cell death, Annu. Rev. Immunol., 1998, vol. 16, pp. 395-419.
Chattergoon, M. A., et al., "Targeted antigen delivery to antigen-presenting cells including dendritic cells by engineered Fas-mediated apoptosis," Nat. Biotechnol., 2000, vol. 18, No. 9, pp. 974-979.
Chernysheva, A. D., el al., "T cell proliferation induced by autologous non-T cells is a response to apoptotic cells processed by dendritic cells," J. Immunol., 2002, vol. 169, No. 3, pp. 1241-1250.
Restifo, N. P., "Building better vaccines: how apoptotic cell death can induce inflammation and activate innate and adaptive immunity," Curr. Opin. Immunol., 2000, vol. 12, No. 5, pp. 597-603.
Sasaki, S. et al., "Apoptosis-mediated enhancement of DNA-raised immune responses by mutant caspases," Nat. Biotechnol., 2001, vol. 19, No. 6, pp. 543-547.
Tisch, R. et al., "Antigen-specific mediated suppression of beta cell autoimmunity by plasmid DNA vaccination," J. Immunol., 2001, vol. 166, No. 3, pp. 2122-2132.
Klinman, D. et al., "Use of CpG oligodeoxynucleotides as immune adjuvants," Imm. Rev., 2004, vol. 199, pp. 201-216.
Krieg, Arthur M., "The role of CpG motifs in innate immunity," Curr. Opin. Immun., 2000, vol. 12, pp. 35-43.
Li, Alice et al., "Co-delivery of pro-apoptotic BAX with a DNA vaccine recruits dendritic cells and promotes efficacy of autoimmune diabetes prevention in mice," Vaccine 22 (2004) pp. 1751-1763.
Li, Alice et al., "Pro-apoptotic DNA vaccination ameliorates new onset of autoimmune diabetes in NOD mice and induces foxp3+ regulatory T cells in vitro," Vaccine 24 (2006) pp. 5036-5046.
Scheule, R. K., "The role of CpG motifs in immunostimulation and gene therapy," Adv. Drug Delivery Rev., 2000, vol. 44, pp. 119-134.
International Search Report and Written Opinion issued in related International Patent Application No. PCT/US06/17763 on Sep. 20, 2007.

* cited by examiner

*Primary Examiner*—Anne Marie S Wehbe
(74) *Attorney, Agent, or Firm*—David A. Farah; Sheldon Mak Rose & Anderson

(57) ABSTRACT

A substance for preventing, delaying the onset of, or treating one or more than one autoimmune disease, the substance comprising a polynucleotide construct comprising a polynucleotide sequence encoding the pro-apoptotic protein BAX and encoding one or more than one autoantigen for the autoimmune disease. A method for preventing, delaying the onset of or treating an autoimmune disease in a patient comprising selecting a patient who is susceptible to developing the autoimmune disease, who is developing the autoimmune disease or who has the autoimmune disease and administering to the patient one or more than one dose of a polynucleotide construct comprising a polynucleotide sequence encoding the pro-apoptotic protein BAX and encoding one or more than one autoantigen for an autoimmune disease, or comprising a polynucleotide sequence encoding the adenoviral protein E3-GP19k, or comprising a polynucleotide sequence encoding ΔBCL-2.

7 Claims, 2 Drawing Sheets

SUBSTANCES FOR PREVENTING AND TREATING AUTOIMMUNE DISEASES

CROSS-REFERENCE TO RELATED APPLICATION

Figure 1:
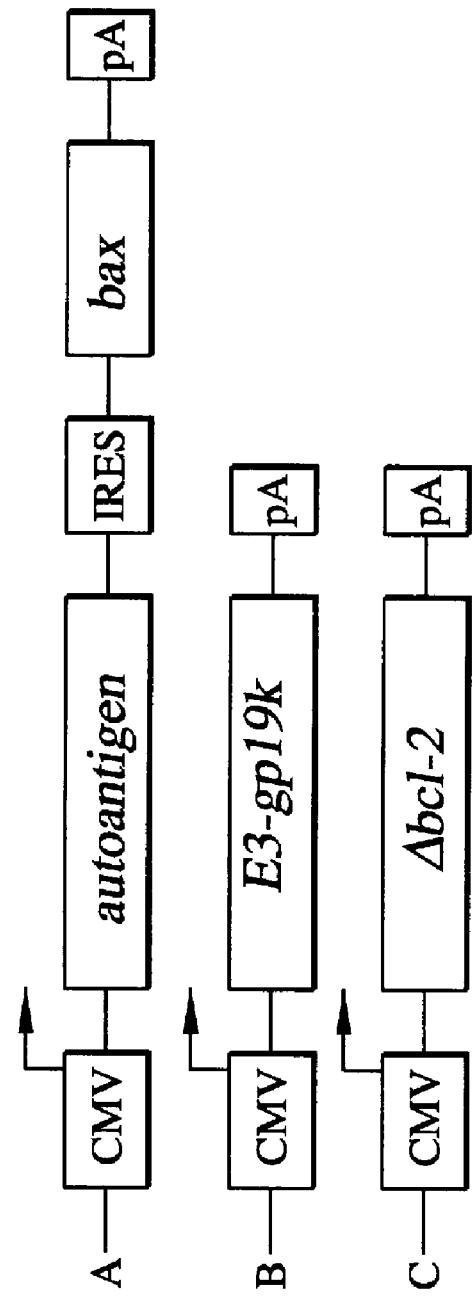

The present Application is a divisional of U.S. patent application Ser. No. 10/523,655, titled "Substances for Preventing and Treating Autoimmune Diseases," filed Feb. 4, 2005, and issued as U.S. Pat. No. 7,381,711 on Jun. 3, 2008, which is a 371 of International Patent Application No. PCT/US03/24625, titled "Substances for Preventing and Treating Autoimmune Diseases," filed Aug. 6, 2003, which claims the benefit of U.S. Provisional Patent Application No. 60/401,652, titled "Method and Substances for the Suppression of Diabetes," filed Aug. 6, 2002, the contents of which are incorporated in this disclosure by reference in their entirety.

STATEMENT REGARDING FEDERALLY SPONSORED RESEARCH OR DEVELOPMENT

This invention was made with United States Government support under Cooperative Agreement Number DAMD-17-97-2-7016 with the National Medical Technology Testbed, Inc., United States Department of the Army. The United States Government has certain rights in this invention.

BACKGROUND

Autoimmune diseases cause significant human morbidity and mortality. These diseases include approximately 80 diseases, such as rheumatoid arthritis, systemic lupus and multiple sclerosis, and affect approximately 5% of the population of the United States. One autoimmune disease, type 1 diabetes, is the most frequent chronic disease in children, and has a steadily increasing worldwide incidence.

Generally, the onset of type 1 diabetes begins with the display by antigen presenting cells (APCs) of autoantigens synthesized by pancreatic beta cells. This display results in the immune system destruction of pancreatic beta cells mediated mostly by T helper 1 (Th1) and cytotoxic T lymphocytes and, thereby, to the loss of insulin production.

Many prophylactic and therapeutic approaches for type 1 diabetes attempt to prevent the destruction of beta cells by inducing the immune system to delete, inactivate or suppress pathogenic self-reactive lymphocytes, such as by administering vaccines that solely deliver autoantigen, or by administering substances are direct effectors of the immune system, such as cytokines. However, currently available DNA-based vaccines are not completely efficient in preventing the disease, and the use of some of these vaccines are associated with inducing or enhancing autoimmunity rather than preventing the disease. Additionally, the use of cytokines is associated with significant morbidity.

Therefore, there is a need for a new method for preventing, delaying the onset of, or treating autoimmune diseases using vaccines that are not associated with these disadvantages. Further, there is a need for a new method for preventing, delaying the onset of, or treating type 1 diabetes using vaccines that are not associated with these disadvantages.

SUMMARY

According to one embodiment of the present invention, there is provided a substance for preventing, delaying the onset of or treating one or more than one autoimmune disease. The substance comprises a polynucleotide construct comprising a polynucleotide sequence encoding the pro-apoptotic protein BAX and encoding one or more than one autoantigen for the autoimmune disease.

According to another embodiment of the present invention, there is provided a use of a polynucleotide construct comprising a polynucleotide sequence encoding the pro-apoptotic protein BAX and encoding one or more than one autoantigen for an autoimmune disease for the manufacture of a medicament for preventing, delaying the onset of or treating the one or more than one autoimmune disease.

According to another embodiment of the present invention, there is provided a use of a polynucleotide construct comprising a polynucleotide sequence encoding the adenoviral protein E3-GP19k for the manufacture of a medicament for preventing, delaying the onset of or treating one or more than one autoimmune disease.

According to another embodiment of the present invention, there is provided a use of a polynucleotide construct comprising a polynucleotide sequence encoding ΔBCL-2 for the manufacture of a medicament for preventing, delaying the onset of or treating one or more than one autoimmune disease.

In one embodiment, the medicament is manufactured in dosage units of between about 0.5 mg to about 5 mg. In another embodiment, the medicament is manufactured in dosage units of between about 1 mg to about 4 mg. In another embodiment, the medicament is manufactured in dosage units of between about 2.5 mg to about 3 mg. In another embodiment, the medicament is manufactured in a form suitable for intramuscular administration. In another embodiment, the medicament is manufactured in a form suitable for intravenous administration.

According to another embodiment of the present invention, there is provided a method for preventing, delaying the onset of or treating an autoimmune disease in a patient. The method comprises selecting a patient who is susceptible to developing the autoimmune disease, who is developing the autoimmune disease or who has the autoimmune disease; and administering to the patient one or more than one dose of a polynucleotide construct comprising a polynucleotide sequence encoding the pro-apoptotic protein BAX and encoding one or more than one autoantigen for the autoimmune disease, or a polynucleotide construct comprising a polynucleotide sequence encoding the adenoviral protein E3-GP19k, or a polynucleotide construct comprising a polynucleotide sequence encoding ΔBCL-2, or a combination of the preceding polynucleotide constructs.

In one embodiment, the autoimmune disease is type I diabetes. In another embodiment, selecting the patient comprises identifying in the patient the presence of anti-insulin or anti-GAD autoantibodies or both anti-insulin and anti-GAD autoantibodies. In another embodiment, selecting the patient comprises identifying in the patient the presence of increasing hyperglycemia. In another embodiment, selecting the patient comprises identifying in the patient the presence of glycosuria. In another embodiment, selecting the patient comprises identifying in the patient the presence of a genetic predisposition to the autoimmune disease.

In another embodiment, the one or more than one dose is a plurality of doses. In another embodiment, administering to the patient one or more than one dose comprises injecting the patient intramuscularly with the one or more than one dose. In another embodiment, the method further comprises, after administering, monitoring the patient for the development of the autoimmune disease.

FIGURES

Figure 2:
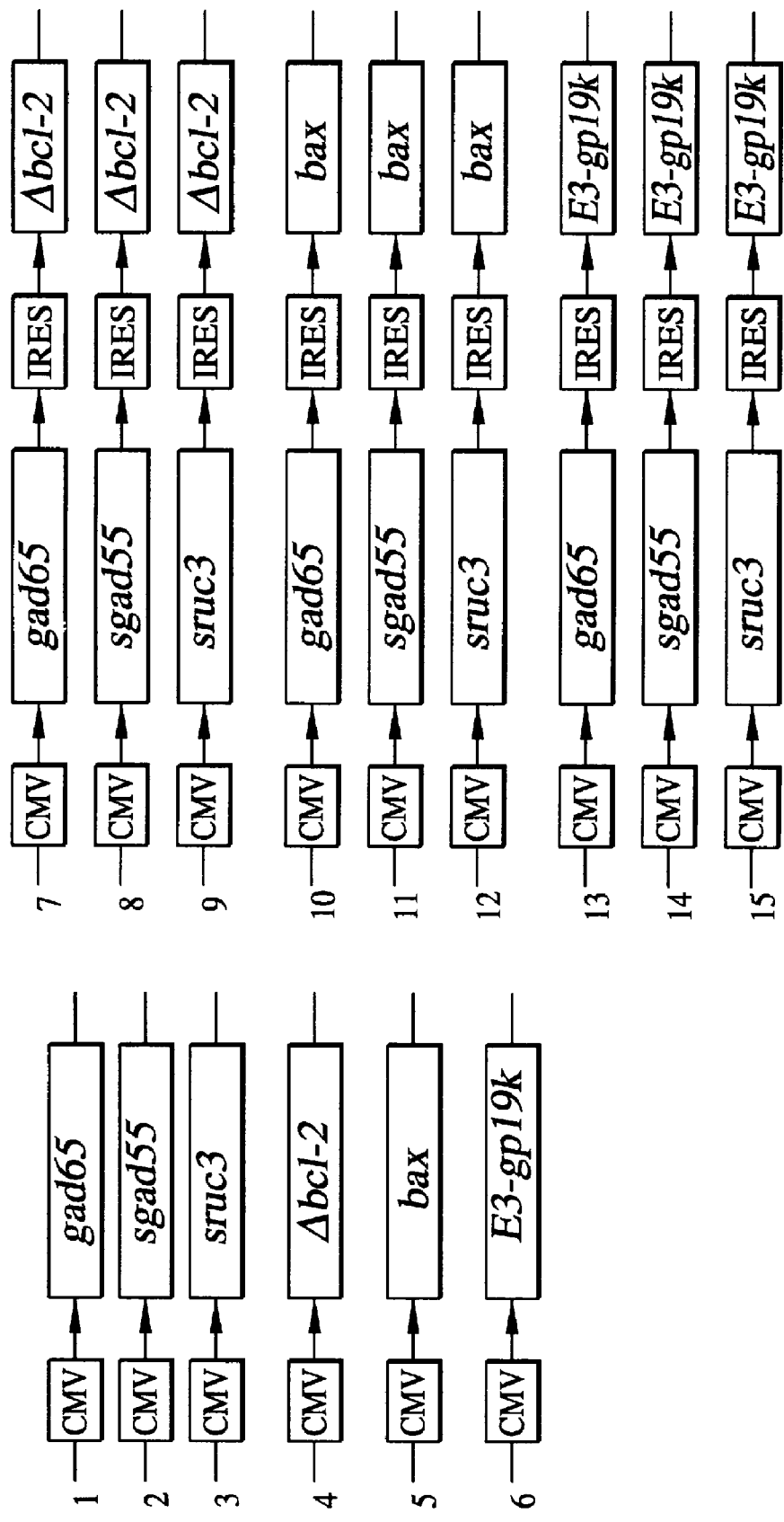

These and other features, aspects and advantages of the present invention will become better understood with regard to the following description, appended claims, and accompanying figures where:

FIG. 1 are schematic depictions of three substances according to the present invention; and FIG. 2 are schematic depictions of the fifteen plasmids that were tested for their efficiency in preventing, delaying the onset of or treating an autoimmune disease in accordance with a method of the present invention.

DESCRIPTION

According to one embodiment of the present invention, there are provided substances for preventing, delaying the onset of or treating one or more than one autoimmune disease. According to another embodiment of the present invention, there is provided a method of preventing, delaying the onset of or treating one or more than one autoimmune disease. In one embodiment, the autoimmune disease is type 1 diabetes. In a preferred embodiment, the method comprising using a substance according to the present invention is a vaccine. The substances and method of the present invention do not use solely the delivery of autoantigen, and do not use molecules that are direct effectors of the immune system as in prior methods. Instead, the present invention uses a vaccine to prevent apoptosis of one or more than one type of cell capable of the suppressing the autoimmune disease. Because these one or more than one type of cell capable of suppressing the autoimmune disease are still be subject to physiological and immune regulation, the risk of inducing or enhancing autoimmunity is greatly reduced by the present method as compared to some prior art methods. Further, because the present invention does not involve administering substances that are direct effectors of the immune system, such as cytokines, the present invention does not pose the risk side effects associated with such direct effectors of the immune system. Further advantageously, a genetic vaccine comprising primarily plasmid DNA can be produced in large quantities at relatively low cost and does not require a "cold chain" for storage. Therefore, the substances and methods according to the present invention are both economical and practical for use to prevent, delay the onset of or treat an autoimmune disease. Further, a genetic vaccine according to the present invention modifies the genetic material of an organism directly which means that native epitopes will be processed by the organism's immune system unlike protein-based vaccines. The substances and method of the present invention will now be disclosed in detail.

As used in this disclosure, the term "autoimmune disease" comprises both diseases due in part or in total to destruction of normal cells or tissues by the organism's own immune system, and also comprises destruction of cells or tissues that were transplanted into the organism to take the place of defective or absent cells or tissues, such as islet cell transplants, or partial or whole organ transplants, by the organism's own immune system.

As used in this disclosure, the term "comprise" and variations of the term, such as "comprising" and "comprises," are not intended to exclude other additives, components, integers or steps.

In one embodiment, the present invention includes three substances that can be used either individually, sequentially or simultaneously to prevent, delay the onset of or treat one or more than one autoimmune disease. One of the three substances is a DNA construct comprising a polynucleotide sequence, SEQ ID NO:1, encoding the pro-apoptotic protein BAX, and encoding one or more than one autoantigen for the autoimmune disease. Another of the three substances is a DNA construct comprising a polynucleotide sequence, SEQ ID NO:2, encoding the adenoviral protein E3-GP19k, which prevents presentation of an antigen on MHC-I molecules in the endoplasmic reticulum. Another of the three substances is a DNA construct comprising a polynucleotide sequence, SEQ ID NO:3, encoding a truncated form of BCL-2 designated ΔBCL-2 in this disclosure.

As will be understood by those with skill in the art with reference to this disclosure, though specific sequences are given for the polynucleotide sequences as disclosed in this disclosure, such as the polynucleotide sequences encoding the pro-apoptotic protein BAX, the adenoviral protein E3-GP19k and ΔBCL-2, the present invention includes any other sequence that does not cause a change in the translated amino acid sequence, as well as any sequence that does cause a change in the translated amino acid sequence but where the change does not substantially affect the function of the translated amino acid sequence so as to make it unsuitable for the uses contemplated in this disclosure.

Referring now to FIG. 1, there are shown schematic depictions of three substances according to the present invention. As can be seen, each substance comprises a plasmid DNA construct. Substance A comprises a plasmid construct comprising a polynucleotide encoding an autoantigen for the autoimmune disease, such as secreted glutamic acid decarboxylase that is an autoantigen for type 1 diabetes, followed by a polynucleotide, SEQ ID NO:1, encoding BAX. Substance B comprises a plasmid construct comprising a polynucleotide, SEQ ID NO:2, encoding E3-GP19k without a polynucleotide encoding an autoantigen for the autoimmune disease. Substance C comprises a plasmid construct comprising a polynucleotide, SEQ ID NO:3, encoding a truncated form of the anti-apoptotic protein BCL-2 without a polynucleotide encoding an autoantigen for the autoimmune disease. As used in the Figures, "CMV" represents the cytomegalovirus promoter element, "pA" represents a polyadenylation site, and "IRES" represents an internal ribosome binding site from the EMCV virus, SEQ ID NO:4.

In order to demonstrate the advantages of the present invention, fifteen plasmids were constructed and used as vaccines. Each construct was cloned into the vector pND2. Referring now to FIG. 2, there are shown schematic depictions of the fifteen plasmids that were tested for their efficiency in preventing, delaying the onset of or treating an autoimmune disease. As can be seen, each plasmid was under the plasmid transcriptional control of the same promoter (CMVp) to ensure expression of both open reading frames in each transfected cells. During construction of these plasmids containing the cDNA encoding BCL-2, it was found that plasmid deletions occurred due to the large size of the cDNA. Therefore, a truncated version of bcl-2 designated Δbcl-2 was used to construct the plasmids. As shown in FIG. 2, the plasmids comprised cDNA encoding cytoplasmic GAD, SEQ ID NO:5, (plasmid 1); secreted GAD (SGAD), SEQ ID NO:6, (plasmid 2); a control secreted luciferase, SEQ ID NO:7, (plasmid 3); truncated human anti-apoptotic protein BCL-2 (ΔBCL-2), SEQ ID NO:3, (plasmid 4); anti-apoptotic protein BAX, SEQ ID NO:1, (plasmid 5); E3-GP19k, SEQ ID NO:2, (plasmid 6); ΔBCL-2, SEQ ID NO:3, in combination with cytoplasmic GAD, SEQ ID NO:5, secreted GAD, SEQ ID NO:62, and secreted luciferase, SEQ ID NO:7, (plasmids 7-9, respectively), BAX, SEQ ID NO:1, in combination with cytoplasmic GAD, SEQ ID NO:5, secreted GAD, SEQ ID NO:6, and secreted luciferase, SEQ ID NO:7, (plasmids 10-12, respectively); and E3-GP19k, SEQ ID NO:2, in combination with cytoplasmic GAD, SEQ ID NO:5, secreted GAD, SEQ ID NO:6, and secreted luciferase, SEQ ID NO:7, (plasmids 13-15, respectively).

All plasmids were generated, the open reading frame amplified using PCR, and the amplification products were inspected after DNA sequencing and found to be without mutations. Each construct was then used to transfect simian COS-7 cells transiently for immunoblot analysis of cell lysates, which confirmed that a gene product of the correct size was encoded (data not shown).

Next, the effects of the 15 plasmids on non-obese diabetic (NOD) mice were determined as follows. First, plasmid DNA was isolated using Qiagen Endofree kits (Qiagen Inc., Chatsworth, Calif., US), and 300 ug of each of the 15 plasmid DNAs was injected intramuscularly into groups of fifteen 4-5-week-old female NOD mice. The 300 ug dose was selected as a dose relevant to the human clinical setting based on organism weight. The onset of diabetes was monitored until the age of 35 weeks, using urine and blood glucose analysis. The mice were considered diabetic after testing positive for high levels of glycosuria, with blood glucose levels greater than 300 mg/dl on two consecutive days.

The results of these experiments demonstrated the following. The percentage of diabetic animals at 35 weeks of age ranged from 73-93% for mice vaccinated with plasmids 1-3; 60-67% for mice vaccinated with plasmids 4 or 7-9; 47-85% for mice vaccinated with plasmids 5 and 10-12; and 53-73% for mice vaccinated with plasmids 6 and 13-15. Control animals (those not vaccinated) had an incidence of diabetes of about 93%. Therefore, administration of 300 ug of plasmid vector alone or of 300 ug of plasmid vector encoding antigens alone, plasmids 1-3, did not result in significant diabetes suppression. Mice vaccinated with plasmids 6-9 and 11 showed statistically significant suppression of diabetes when compared to untreated mice (P<0.05 for plasmid 7, and P<0.02 for plasmid 9). In addition, mice receiving pND2-E3-GP19k, plasmid 6 or pND2-SGAD55-BAX, plasmid 11 showed a significantly decreased incidence of diabetes at 35 weeks when compared to mice receiving plasmid pND2-GAD65, plasmid 1 or pND2-GAD65-BAX, plasmid 10 (P<0.04), and mice receiving pND2-GAD65-ΔBCL2, plasmid 7 or pND2-SGAD55-ΔBCL2, plasmid 8 showed significantly decreased diabetes when compared to mice receiving pND2-GAD65, plasmid 1 (P<0.05). Suppression of diabetes was associated with decreased islet inflammation (data not shown). These results will be disclosed now in greater detail.

Mice that were vaccinated with plasmids comprising Δbcl-2, plasmids 4 and 7-9, showed a 4-5 weeks delay in diabetes onset regardless of the co-expressed antigen, and a decrease in the incidence of diabetes at 35 weeks of age (60-67% compared to about 93% for the unvaccinated control mice) regardless of the co-expressed antigen. Therefore, co-expression of GAD autoantigen did not suppress the effect.

Mice that were vaccinated with plasmids comprising bax, plasmids 5 and 10-12, did not show diabetes suppression, with the exception of sgad55-bax, plasmid 11. While mice vaccinated with plasmid 11 started to develop diabetes at a time similar to other mice vaccinated with a plasmid comprising only bax, plasmid 5, the incidence of diabetes in mice vaccinated with plasmid 11 at 35 weeks of age was only 47% compared with a 93% incidence for the unvaccinated control mice (p<0.05).

Mice that were vaccinated with plasmids comprising E3-gp19k, plasmids 6 and 13-15 showed wide differences in diabetes onset, depending on the antigen that was co-expressed. Mice that were vaccinated with the plasmid comprising E3-gp19k without autoantigen, plasmid 6 started to develop diabetes with a 4-5 week delay, and showed decreased diabetes at 35 weeks of age (53% vs 93% for the unvaccinated control mice for control) (p<0.05). Mice that were vaccinated with the plasmids comprising E3-gp19k with autoantigen, plasmids 13-15, suppressed the effect, both with respect to the delay in the onset of diabetes and with respect to the incidence of diabetic animals at 35 weeks.

Next, immune responses were characterized using a GAD-specific ELISpot assay and ELISA of serum anti-GAD IgG isotypes to determine whether diabetes suppression by the administration of the substances of the present invention was associated with suppression of inflammatory Th1-like activity, and up-regulation of anti-inflammatory Th2 like response.

The ELISpot assay was conducted as follows. Splenocytes were isolated from the mice at time of diabetes onset, or at the end of the observation period for non-diabetic animals. The cells were then stimulated with recombinant GAD protein, and the number of cells secreting IFN-gamma (for Th1-like activity), and IL-4 (for Th2-like activity) were counted, following a standard manufacturer's protocol. The number of cells secreting the cytokines in the absence of GAD stimulation was then subtracted, and results analyzed. For IFN-gamma the data clearly indicated that suppression of diabetes by plasmid 6, encoding E3-GP19k alone, or by plasmids 4 and 7-9, encoding ΔBCL-2 alone or together with an antigen, were associated with a suppression of GAD-specific activity. Therefore, E3-19k and ΔBCL-2 could induce an immune response that was able to suppress autoreactivity against beta cells. Surprisingly, the SGAD55-BAX combination did not appear to significantly suppress Th1-like activity. Further, SGAD55 alone, which did not suppress diabetes, did suppress GAD-specific Th1-like response.

With respect to IL-4, the data indicated an increase in GAD-specific activity for mice that received plasmid 6 encoding E3-GP19k alone (diabetes suppression), plasmid 13 encoding SGAD55 and E3-19k (no diabetes suppression), and plasmid 8 SGAD55 and ΔBCL-2 (diabetes suppression). Thus, increased Th2-like activity was not always associated with decreased Th1-like activity or disease suppression.

The ELISA was conducted as follows. Animal sera were used for ELISA of anti-GAD IgG2a,b and IgG1 isotypes, which indicate a Th1-like and Th2-like activity, respectively. ELISA of anti-GAD IgG2a,b indicated that three of the plasmid DNAs coding for ΔBCL-2, plasmids 4, 8 and 9, showed a significant reduction in Th1-like activity, when compared to plasmid 5 coding for BAX, but not with the unvaccinated control mice. ELISA of anti-GAD IgG1 indicated that all plasmid DNAs encoding BAX, plasmids 5 and 10-12, resulted in decreased Th2-like activity.

These data taken together indicate that, first, bax, a plasmid cDNA coding for a pro-apoptotic protein, can be used as a molecular adjuvant for genetic vaccines to prevent autoimmune disease, such as a vaccine comprising a polynucleotide encoding a secreted form of an autoantigen. Second, a plasmid cDNA encoding E3-GP19k or encoding a truncated BCL-2 alone could suppress autoimmune disease, though a plasmid cDNA encoding E3-GP19k or encoding a truncated BCL-2 combined with an autoantigen was less effective.

In one embodiment of the present invention, there is provided a method of preventing, delaying the onset of or treating an autoimmune disease. The method comprises, first, selecting a patient who is susceptible to developing the autoimmune disease, who is developing the autoimmune disease or who has the autoimmune disease. The selection can be made using standard methods as will be understood by those with skill in the art with reference to this disclosure. For example, if the autoimmune disease is diabetes, the selection can be made by identifying in the patient the presence of anti-insulin or anti-GAD autoantibodies or both anti-insulin and/or anti-GAD autoantibodies, the presence of increasing hyperglycemia, the presence of glycosuria, the presence of a genetic predisposition to diabetes or more than one of these.

Next, the patient is administered one or more than one dose of a plasmid construct according to the present invention. That is, a plasmid construct comprising a polynucleotide encoding an autoantigen for the autoimmune disease and encoding BAX, or a plasmid construct comprising a polynucleotide encoding E3-GP19k but without a polynucleotide encoding an autoantigen for the autoimmune disease, or a plasmid construct comprising a polynucleotide encoding a truncated form of the anti-apoptotic protein BCL-2 but without a polynucleotide encoding an autoantigen for the autoimmune disease. In a preferred embodiment, the organism is administered two plasmid constructs according to the present invention. In a particularly preferred embodiment, the organism is administered all three plasmid constructs according to the present invention.

In a preferred embodiment, the plasmid construct is administered in a plurality of doses. In another preferred embodiment, the dose is between about 0.001 mg/Kg and about 10 mg/Kg. In another preferred embodiment, the dose is between about 0.01 mg/Kg and about 1 mg/Kg. In another preferred embodiment, the dose is about 0.05 mg/Kg. In a preferred embodiment, a suitable dose for a human adult is between about 0.5 mg and 5 mg. In a preferred embodiment, a suitable dose for a human adult is between about 1 mg and 4 mg. In a preferred embodiment, a suitable dose for a human adult is between about 2.5 mg and 3 mg. In another preferred embodiment, the dose is administered weekly between about 2 and about 10 times. In a particularly preferred embodiment, the dose is administered weekly 4 times. In another particularly preferred embodiment, the dose is administered only once.

Administration can be by a suitable route. In a preferred embodiment, the route is intramuscular or intravenous.

Additionally, the method can comprise, after administering, monitoring the patient for the development of the autoimmune disease.

EXAMPLE I

Prevention of Diabetes

According to the present invention, the onset of diabetes in a patient is delayed or prevented, for example, as follows. First, the patient is selected based on the presence of circulating anti-insulin and anti-GAD autoantibodies. Next, the patient is injected intramuscularly with 0.05 mg/Kg of a plasmid construct comprising a polynucleotide sequence, SEQ ID NO:1, encoding the pro-apoptotic protein BAX and encoding SGAD, SEQ ID NO:6, or comprising a polynucleotide sequence, SEQ ID NO:2, encoding the adenoviral protein E3-GP19k, or comprising a polynucleotide sequence, SEQ ID NO:3, encoding ΔBCL-2. The injection is repeated weekly for 3 weeks while the level of circulating anti-insulin and anti-GAD autoantibodies is monitored. The treatment is ended when the level of circulating anti-insulin and anti-GAD autoantibodies has returned to normal.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. A method for delaying the onset of or inhibiting the development of type I diabetes in a patient comprising:
   a) selecting a patient who is susceptible to developing type I diabetes, who is developing type I diabetes or who has type I diabetes; and
   b) administering to the patient by intramuscular injection one or more than one dose of a polynucleotide sequence of SEQ ID NO:3 encoding the adenoviral protein ΔBCL-2 operably linked with a CMV promoter.

2. The method of claim 1, where selecting the patient comprises identifying in the patient the presence of anti-insulin or anti-GAD autoantibodies or both anti-insulin and anti-GAD autoantibodies.

3. The method of claim 1, where selecting the patient comprises identifying in the patient the presence of increasing hyperglycemia.

4. The method of claim 1, where selecting the patient comprises identifying in the patient the presence of glycosuria.

5. The method of claim 1, where selecting the patient comprises identifying in the patient the presence of a genetic predisposition to type I diabetes.

6. The method of claim 1, where the one or more than one dose is a plurality of doses.

7. The method of claim 1, further comprising, after administering, monitoring the patient for the development of type I diabetes.

* * * * *

SEQUENCE LISTING

<160> NUMBER OF SEQ ID NOS: 7

<210> SEQ ID NO 1
<211> LENGTH: 579
<212> TYPE: DNA
<213> ORGANISM: Homo sapiens

<400> SEQUENCE: 1

```
atggacgggt ccggggagca gcccagaggc ggggggccca ccagctctga gcagatcatg      60
aagacagggg ccctttgct tcagggtttc atccaggatc gagcagggcg aatggggggg     120
gaggcacccg agctggccct ggacccggtg cctcaggatg cgtccaccaa gaagctgagc     180
gagtgtctca agcgcatcgg ggacgaactg gacagtaaca tggagctgca gaggatgatt     240
gccgccgtgg acacagactc cccccgagag gtcttttcc gagtggcagc tgacatgttt     300
tctgacggca acttcaactg gggccgggtt gtcgcccttt tctactttgc cagcaaactg     360
gtgctcaagg ccctgtgcac caaggtgccg gaactgatca gaaccatcat gggctggaca     420
ttggacttcc tccgggagcg gctgttgggc tggatccaag accagggtgg ttgggacggc     480
ctcctctcct actttgggac gcccacgtgg cagaccgtga ccatctttgt ggcgggagtg     540
ctcaccgcct cgctcaccat ctggaagaag atgggctga                           579
```

<210> SEQ ID NO 2
<211> LENGTH: 492
<212> TYPE: DNA
<213> ORGANISM: Human adenovirus type 2

<400> SEQUENCE: 2

```
atgaggtaca tgattttagg cttgctcgcc cttgcggcag tctgcagcgc tgccaaaaag      60
gttgagttta aggaaccagc ttgcaatgtt acatttaaat cagaagctaa tgaatgcact     120
actcttataa aatgcaccac agaacatgaa aagcttatta ttcgccacaa agacaaaatt     180
ggcaagtatg ctgtatatgc tatttggcag ccaggtgaca ctaacgacta taatgtcaca     240
gtcttccaag gtgaaaatcg taaaacttt atgtataaat ttccatttta tgaaatgtgc      300
gatattacca tgtacatgag caaacagtac aagttgtggc ccccacaaaa gtgtttagag     360
aacactggca ccttttgttc caccgctctg cttattacag cgcttgcttt ggtatgtacc     420
ttactttatc tcaaatacaa aagcagacgc agttttattg atgaaaagaa aatgccttga     480 tttttccgctt gc                                                        492
```

<210> SEQ ID NO 3
<211> LENGTH: 599
<212> TYPE: DNA
<213> ORGANISM: Homo sapiens

<400> SEQUENCE: 3

```
atggcgcacg ctgggagaag tggttacgat aaccgggaga tagtgatgaa gtacatccat      60
tataagctgt cgcagagggg ctacgagtgg gatgctaccg cggctgccgc ggggcctgcg     120
ctcagcccgg tgccacctgt ggtccacctg accctccgcc aggccggcga cgacttctcc     180
cgccgctacc gccgcgactt cgccgagatg tccagccagc tgcacctgac gcccttcacc     240
gcgcggggat gctttgccac ggtggtggag gagctcttca gggacggggt gaactggggg     300
aggattgtgg ccttctttga gttcggtggg gtcatgtgtg tggagagcgt caaccgggag     360
atgtcgcccc tggtggacaa catcgccctg tggatgactg agtacctgaa ccggcacctg     420
cacacctgga tccaggataa cggaggctgg gatgcctttg tggaactgta cggccccagc     480
atgcggcctc tgtttgattt ctcctggctg tctctgaaga ctctgctcag tttggccctg     540
gtgggagctt gcatcaccct gggtgcctat ctgggccaca gtgaagtca acatgcctg      599
```

<210> SEQ ID NO 4
<211> LENGTH: 619
<212> TYPE: DNA
<213> ORGANISM: Encephalomyocarditis virus

<400> SEQUENCE: 4

```
tctagataat acgactcact atagggcgaa ttccccctct ccctccccc ccctaacgt        60 tactggccga agccgcttgg aataaggccg gtgtgcgttt gtctatatgt tattttccac     120
catattgccg tcttttggca atgtgagggc ccggaaacct ggccctgtct tcttgacgag     180
cattcctagg ggtctttccc ctctcgccaa aggaatgcaa ggtctgttga atgtcgtgaa     240
ggaagcagtt cctctggaag cttcttgaag acaaacaacg tctgtagcga ccctttgcag     300
gcagcggaac cccccacctg cgacaggtg cctctgcggc caaaagccag gtgtataaga      360
tacacctgca aaggcggcac aaccccagtg ccacgttgtg agttggaata gttgtggaaa     420
gagtcaaatg gctctcctca agcgtattca acaaggggct gaaggatgcc cagaaggtac     480
cccattgtat gggatctgat ctggggcctc ggtgcacatg ctttacatgt gtttagtcga     540
```

```
ggttaaaaaa cgtctaggcc ccccaaccac ggggacgtgg ttttcctttg aaaaacacga      600
ttattatatt gcctctaga                                                   619

<210> SEQ ID NO 5
<211> LENGTH: 1868
<212> TYPE: DNA
<213> ORGANISM: Homo sapiens

<400> SEQUENCE: 5
gagctccacc gcggtggcgg ccgctctaga ccaccatggc atctccgggc tctggctttt       60
ggtctttcgg gtcggaagat ggctctgggg attccgagaa tcccggcaca gcgcgagcct      120
ggtgccaagt ggctcagaag ttcacgggcg gcatcggaaa caaactgtgc gccctgctct      180
acggagacgc cgagaagccg gcggagagcg gcgggagcca accccgcgg gccgccgccc       240 ggaaggccgc ctgcgcctgc gaccagaagc cctgcagctg ctccaaagtg gatgtcaact      300
acgcgtttct ccatgcaaca gacctgctgc cggcgtgtga tggagaaagg cccactttgg      360
cgtttctgca agatgttatg aacattttac ttcagtatgt ggtgaaaagt ttcgatagat      420
caaccaaagt gattgatttc cattatccta atgagcttct ccaagaatat aattgggaat      480
tggcagacca accacaaaat ttggaggaaa ttttgatgca ttgccaaaca actctaaaat      540
atgcaattaa acagggcat cctagatact tcaatcaact ttctactggt ttggatatgg      600
ttggattagc agcagactgg ctgacatcaa cagcaaatac taacatgttc acctatgaaa      660
ttgctccagt atttgtgctt ttggaatatg tcacactaaa gaaaatgaga gaaatcattg      720
gctggccagg gggctctggc gatgggatat tttctcccgg tggcgccata tctaacatgt      780
atgccatgat gatcgcacgc tttaagatgt tcccagaagt caaggagaaa ggaatggctg      840
ctcttcccag gctcattgcc ttcacgtctg aacatagtca tttttctctc aagaagggag      900
ctgcagcctt agggattgga agagacagcg tgattctgat taaatgtgat gagagaggga      960
aaatgattcc atctgatctt gaaagaagga ttcttgaagc caaacagaaa gggtttgttc     1020
ctttcctcgt gagtgccaca gctggaacca ccgtgtacgg agcatttgac cccctcttag     1080
ctgtcgctga catttgcaaa aagtataaga tctggatgca tgtggatgca gcttggggtg     1140
ggggattact gatgtcccga aaacacaagt ggaaactgag tggcgtggag agggccaact     1200
ctgtgacgtg gaatccacac aagatgatgg gagtcccttt gcagtggtct gctctcctgg     1260
ttagagaaga gggattgatg cagaattgca accaaatgca tgcctcctac ctctttcagc     1320
aagataaaca ttatgacctg tcctatgaca ctggagacaa ggccttacag tgcgacgcc      1380 acgttgatgt ttttaaacta tggctgatgt ggagggcaaa ggggactacc gggtttgaag     1440
cgcatgttga taaatgtttg gagttggcag agtatttata caacatcata aaaaaccgag     1500
aaggatatga gatggtgttt gatgggaagc ctgaggacac aaatgtctgc ttctggtaca     1560
ttcctccaag cttgcgtact ctggaagaca tgaagagag aatgagtcgc ctctcgaagg     1620
tggctccagt gattaaagcc agaatgatgg agtatgaac cacaatggtc agctaccaac     1680
ccttgggaga caaggtcaat ttcttccgca tggtcatctc aaacccagcg gcaactcacc     1740
aagacattga cttcctgatt gaagaaatag aacgccttgg acaagattta taataacctt     1800
gctcaccaag ctgttccact tctctaggta gcgacctcga gcggccgctc gagggggggc     1860
ccggtacc                                                             1868
```

```
<210> SEQ ID NO 6
<211> LENGTH: 1638
<212> TYPE: DNA
<213> ORGANISM: Artificial
<220> FEATURE:
<223> OTHER INFORMATION: secreted form of human GAD

<400> SEQUENCE: 6
atgtacagga tgcaactcct gtcttgcatt gcactaagtc ttgcacttgt cacaaacagt      60
gcacctactt acgcgtttct ccatgcaaca gacctgctgc cggcgtgtga tggagaaagg     120
cccactttgg cgtttctgca agatgttatg aacattttac ttcagtatgt ggtgaaaagt     180
ttcgatagat caaccaaagt gattgatttc cattatccta atgagcttct ccaagaatat     240
aattgggaat tggcagacca accacaaaat ttggaggaaa ttttgatgca ttgccaaaca     300
actctaaaat atgcaattaa acagggcatc ctagatact tcaatcaact ttctactggt     360
ttggatatgg ttggattagc agcagactgg ctgacatcaa cagcaaatac taacatgttc     420
acctatgaaa ttgctccagt atttgtgctt ttggaatatg tcacactaaa gaaaatgaga     480
gaaatcattg ctggccaggg ggctctggc gatgggatat tttctcccgg tggcgccata     540
tctaacatgt atgccatgat gatcgcacgc tttaagatgt cccagaagt caaggagaaa     600
ggaatggctg ctcttcccag gctcattgcc ttcacgtctg aacatagtca tttttctctc     660
aagaagggag ctgcagcctt agggattgga agagacagcg tgattctgat taaatgtgat     720
gagagaggga aaatgattcc atctgatctt gaaagaagga ttcttgaagc caaacagaaa     780
gggtttgttc ctttcctcgt gagtgccaca gctggaacca ccgtgtacgg agcatttgac     840
cccctcttag ctgtcgctga catttgcaaa aagtataaga tctggatgca tgtggatgca     900
gcttggggtg ggggattact gatgtcccga aaacacaagt ggaaactgag tggcgtggag     960
agggccaact ctgtgacgtg aatccacac aagatgatgg gagtcccttt gcagtggtct    1020
gctctcctgg ttagagaaga gggattgatg cagaattgca accaaatgca tgcctcctac    1080
ctctttcagc aagataaaca ttatgacctg tcctatgaca ctggagacaa ggccttacag    1140
tgcggacgcc acgttgatgt tttaaacta tggctgatgt ggagggcaaa ggggactacc    1200
gggtttgaag cgcatgttga taaatgtttg gagttggcag agtatttata caacatcata    1260
aaaaaccgag aaggatatga gatggtgttt gatgggaagc tgaggacac aaatgtctgc    1320
ttctggtaca ttcctccaag cttgcgtact ctggaagaca tgaagagag aatgagtcgc    1380
ctctcgaagg tggctccagt gattaaagcc agaatgatgg agtatggaac acaatggtc    1440
agctaccaac ccttgggaga caaggtcaat ttcttccgca tggtcatctc aaacccagcg    1500
gcaactcacc aagacattga cttcctgatt gaagaaatag aacgccttgg acaagattta    1560
taataacctt gctcaccaag ctgttccact tctctaggta gcgacctcga gcggccgctc    1620
gagggggggc ccggtacc                                                  1638

<210> SEQ ID NO 7
<211> LENGTH: 1271
<212> TYPE: DNA
<213> ORGANISM: Artificial
<220> FEATURE:
<223> OTHER INFORMATION: secreted form of Renilla luciferase

<400> SEQUENCE: 7
atgtacagga tgcaactcct gtcttgcatt gcactaagtc ttgcacttgt cacaaacagt      60
gcacctactg aattcagctt aaagatgact tcgaaagttt atgatccaga acaaaggaaa     120
```

```
                                    -continued
cggatgataa ctggtccgca gtggtgggcc agatgtaaac aaatgaatgt tcttgattca    180
tttattaatt attatgattc agaaaaacat gcagaaaatg ctgttatttt tttacatggt    240
aacgcggcct cttcttattt atggcgacat gttgtgccac atattgagcc agtagcgcgg    300
tgtattatac cagatcttat tggtatgggc aaatcaggca aatctggtaa tggttcttat    360
aggttacttg atcattacaa atatcttact gcatggtttg aacttcttaa tttaccaaag    420
aagatcattt ttgtcggcca tgattggggt gctgctttgg catttcatta tagctatgag    480
catcaagata agatcaaagc aatagttcac gctgaaagtg tagtagatgt gattgaatca    540
tgggatgaat ggcctgatat tgaagaagat attgcgttga tcaaatctga agaaggagaa    600
aaaatggttt tggagaataa cttcttcgtg gaaaccatgt tgccatcaaa aatcatgaga    660
aagttagaac cagaagaatt tgcagcatat cttgaaccat tcaaagagaa aggtgaagtt    720
cgtcgtccaa cattatcatg gcctcgtgaa atcccgttag taaaaggtgg taaacctgac    780
gttgtacaaa ttgttaggaa ttataatgct tatctacgtg caagtgatga tttaccaaaa    840
atgtttattg aatcggatcc aggattcttt tccaatgcta ttgttgaagg cgccaagaag    900
tttcctaata ctgaatttgt caaagtaaaa ggtcttcatt tttcgcaaga agatgcacct    960
gatgaaatgg gaaaatatat caaatcgttc gttgagcgag ttctcaaaaa tgaacaataa    1020
ttactttggt ttttttattta catttttccc gggtttaata atataaatgt cattttcaac    1080
aattttattt taactgaata tttcacaggg aacattcata tatgttgatt aatttagctc    1140
gaactttact ctgtcatatc attttggaat attacctctt tcaatgaaac tttataaaca    1200
gtggttcaat taattaatat atattataat tacatttgtt atgtaataaa ctcggtttta    1260
ttataaaaaa a                                                        1271
```